US00PP10805P

United States Patent [19]

Man

[11] Patent Number: Plant 10,805

[45] Date of Patent: Feb. 23, 1999

[54] BEGONIA PLANT NAMED 'JULIE'

[75] Inventor: Jan Man, Amstelveen, Netherlands

[73] Assignee: Begonia Breeders Assoc., B.V., Aalsmeer, Netherlands

[21] Appl. No.: 923,729

[22] Filed: Sep. 4, 1997

[51] Int. Cl.[6] ..... A01H 5/00

[52] U.S. Cl. ..... Plt./87.18

[58] Field of Search ..... Plt./87.17, 87.18

*Primary Examiner*—Howard J. Locker
*Assistant Examiner*—Kent L. Bell
*Attorney, Agent, or Firm*—C. A. Whealy

[57] ABSTRACT

A distinct cultivar of Begonia plant named 'Julie', characterized by its attractive bright yellow and red bi-colored fully double flowers that are about 5 cm in diameter; resistance to Powdery Mildew under commercial greenhouse conditions; and excellent postproduction longevity.

1 Drawing Sheet

The present invention relates to a new and distinct cultivar of Begonia plant, botanically known as*Begonia* X *hiemalis*, commercially known as Elatior Begonia, and hereinafter referred to by the cultivar name 'Julie'.

The new cultivar was discovered by the inventor in a controlled environment in Amstelveen, The Netherlands, in 1996, as a naturally-occurring mutation of the nonpatented Elatior Begonia cultivar 'Yutta'. The new cultivar was observed as a single plant in a group of 13-cm flowering plants of the parent cultivar. The selection of this plant was based on its yellow and red bi-colored flowers and more fully double flowers. A detailed comparison of plants of the new Begonia and the cultivar 'Yutta' appears in Chart A at the end of the specification.

Asexual reproduction of the new cultivar by terminal cuttings taken in a controlled environment in Amstelveen, The Netherlands, has shown that the unique features of this new Begonia are stable and reproduced true to type in successive generations.

The cultivar 'Julie' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Julie'. These characteristics in combination distinguish 'Julie' as a new and distinct cultivar:

1. Attractive bright yellow and red bi-colored fully double flowers that are about 5 cm in diameter.
2. Resistance to Powdery Mildew under commercial greenhouse conditions.
3. Excellent postproduction longevity.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical flowering plant of 'Julie'. Flower and foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. the following observations and measurements describe plants grown in Amstelveen, the Netherlands, that were flowered in June/July under commercial practice in a glass-covered greenhouse. Average day temperatures were 20° C. and average night temperatures were 18° C. The maximum light level was 18,000 lux. Measurements and numerical values represent averages for six typical flowering plants.

Botanical classification: *Begonia* X *heimalis* cultivar 'Julie'.

Commercial classification: Elatior Begonia.

Parentage: Naturally-occurring mutation of *Begonia* X *hiemalis* cultivar 'Yutta'.

Propagation:

*Type.*—Terminal cuttings.

*Time to rooting.*—About 14 days with soil temperatures of 23° C.

*Rooting habit.*—Fine, fibrous and well-branched.

Plant description:

*Plant form.*—Upright and rounded potted plant, freely branching with good stem and stem base strength. Flowers are fully double and abundant. Plants flower continuously.

*Growth habit.*—Moderate growth rate and moderately vigorous. Suitabe for 13-cm containers. Under optimal environmental and cultural conditions, usually 10 weeks are required to produce proportional 13-cm potted plants from terminal cuttings. Vegetative shoots are formed at basal nodes and flowering shoots are formed at upper nodes.

*Plant height.*—About 30 cm.

*Plant width.*—About 25 cm.

*Leaves.*—Arrangement: Simple, alternate. Length: About 13 cm. Width: About 11 cm. Shape: Asymmetrically ovate. Apex: Acute. Base: Cordate, overlapping. Margin: Slightly doubly serrate. Texture: Smooth, shiny, leathery. Color: Young foliage: Upper surface: 139A. Lower surface: 138B. Fully expanded foliage: Upper surface: 131A. Lower surface: 138B.

Flower description:

*Flowering habit.*—Fully double flowers arranged in axillary cymes. Many cymes in flower simultaneously. Flowering continuous.

*Natural flowering season.*—Plant will flower year around regardless of daylength, however plant will flower earlier and more abundantly if daylength is 12 hours or less. Usually plant starts flowering after about 7 weeks of start of short day/long night treatments.

*Flowers.*—Shape: Rounded, cupped. Diameter: About 5 cm. Depth (height): About 1 cm.

*Tepals.*—Arrangement: Rosette. Shape: Flat to cupped, rounded with entire margin. Quantity per flower: Usually 14 to 20 per flower. Color: When Opening: Upper surface: Yellow, 5B, at center with red, 44B, at margin. Lower Surface: Yellow, 3D, at center with red, 44B, at margin. Fully opened: Upper surface: Yellow, 5B/6A, at center with red, 44B, at margin. Red margin is 1 to 4 mm in width. Lower surface: Yellow, 3D, at center with red, 44B, at margin. Texture: Smooth, velvety, glabrous.

*Sepals.*—Arrangement: Two, opposite. Color: 144A.

*Reproductive organs.*—Stamens: None. Pistils: None.

Postproduction longevity:

*Individual flowers.*—Generally 2 to 3 weeks.

*Whole plants.*—About 6 weeks under interior conditions.

Disease resistance: Plants of the cultivar Julie are resistant to Powdery Mildew under greenhouse conditions.

Seed production: Seed production has not been observed as reproductive organs are not formed.

CHART A

| CHARACTERISTIC | 'JULIE' | 'YUTTA' |
|---|---|---|
| YOUNG LEAF COLOR, UPPER SURFACE | 139A | 147A |
| YOUNG LEAF COLOR, LOWER SURFACE | 138B | 138B |
| FULLY EXPANDED LEAF COLOR, UPPER SURFACE | 131A | 147A |
| FULLY EXPANDED LEAF COLOR, LOWER SURFACE | 138B | 138B |
| FLOWER FORM | Double | Semi-double |
| FLOWER DIAMETER | About 5 cm | About 5.5 cm |
| NUMBER OF TEPALS | 14 to 20 per flower | 6 to 8 per flower |
| TEPAL COLOR, WHEN OPENING, UPPER SURFACE | Center: 5B<br>Margin: 44B | Center: 2C<br>Margin: 33B |
| TEPAL COLOR, WHEN OPENING, LOWER SURFACE | Center: 3D<br>Margin: 44B | Center: 1D<br>Margin: 33B |
| TEPAL COLOR, FULLY OPENED, UPPER SURFACE | Center: 5B/6A<br>Margin: 44B | Center: 2C/4B<br>Margin: 33B |
| TEPAL COLOR, FULLY OPENED, LOWER SURFACE | Center: 3D<br>Margin: 44B | Center: 1D<br>Margin: 33B |
| WIDTH OF TEPAL MARGIN, FULLY OPENED, UPPER SURFACE | 1 to 4 mm | 0.5 to 2 mm |

It is claimed:

1. A new and distinct culivar of Begonia plant named 'Julie', as illustrated and described.

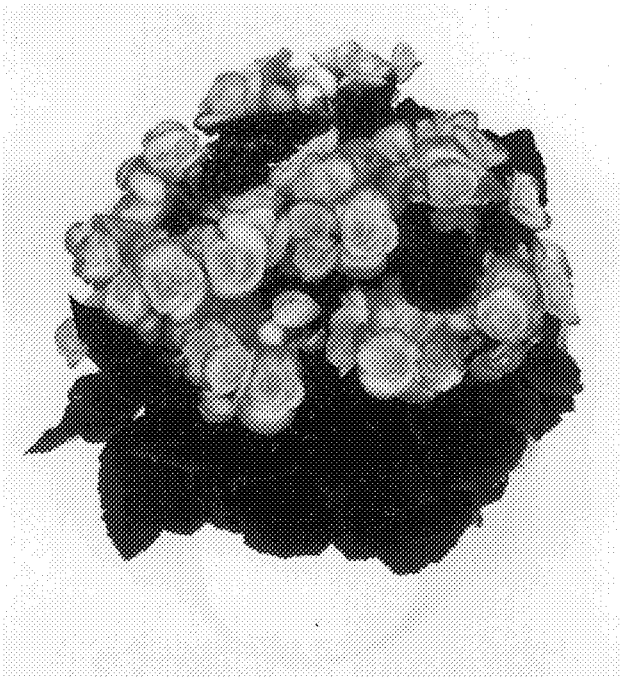

* * * * *